(12) United States Patent
Barker

(10) Patent No.: US 8,267,855 B2
(45) Date of Patent: Sep. 18, 2012

(54) MEDICAL INSTRUMENTS

(75) Inventor: Stephen George Edward Barker, London (GB)

(73) Assignee: Evexar Medical Limited, London (GB)

(*) Notice: Subject to any disclaimer, the term of this patent is extended or adjusted under 35 U.S.C. 154(b) by 531 days.

(21) Appl. No.: 12/598,911

(22) PCT Filed: May 2, 2008

(86) PCT No.: PCT/GB2008/001532
§ 371 (c)(1),
(2), (4) Date: Nov. 19, 2009

(87) PCT Pub. No.: WO2008/135737
PCT Pub. Date: Nov. 13, 2008

(65) Prior Publication Data
US 2010/0094092 A1    Apr. 15, 2010

(30) Foreign Application Priority Data
May 4, 2007  (GB) .................................. 0708761.2

(51) Int. Cl.
*A61B 1/07* (2006.01)
*A61B 1/012* (2006.01)
(52) U.S. Cl. .................. 600/182; 600/179; 600/177
(58) Field of Classification Search .......... 600/154–155, 600/177, 179, 182
See application file for complete search history.

(56) References Cited

U.S. PATENT DOCUMENTS

| | | | |
|---|---|---|---|
| 1,703,216 A * | 2/1929 | Wappler | 600/171 |
| 2,896,611 A | 7/1959 | Moore | |
| 3,373,736 A * | 3/1968 | Fiore et al. | 600/121 |
| 3,417,746 A * | 12/1968 | Moore et al. | 600/184 |
| 3,675,641 A | 7/1972 | Fiore | |
| 4,067,323 A | 1/1978 | Troutner et al. | |
| 4,157,709 A * | 6/1979 | Schuster et al. | 600/572 |
| 4,215,678 A | 8/1980 | Heine et al. | |
| 4,619,248 A | 10/1986 | Walsh | |
| 5,465,709 A | 11/1995 | Dickie et al. | |
| 5,499,964 A | 3/1996 | Beck et al. | |
| 5,785,648 A | 7/1998 | Min | |
| 6,024,697 A | 2/2000 | Pisarik | |
| 6,048,308 A | 4/2000 | Strong | |
| 6,432,049 B1 | 8/2002 | Banta | |
| 6,447,444 B1 * | 9/2002 | Avni et al. | 600/121 |

(Continued)

FOREIGN PATENT DOCUMENTS

GB    25040    0/1913

(Continued)

*Primary Examiner* — Clayton E Laballe
*Assistant Examiner* — Leon W Rhodes, Jr.
(74) *Attorney, Agent, or Firm* — Jones, Walker, Waechter, Poitevent, Carrere & Denegre L.L.P.

(57) ABSTRACT

An illuminated medical instrument comprises an insertion portion (1) for insertion into a body opening and defining an elongate passageway (2), the passageway extending along a longitudinal axis (3) and having a proximal end (4) and a distal end (5). An obturator (19) is fitted into the passageway (2). A light emitting structure (7) has a distal end arranged to direct light from the insertion portion (1) into the body opening. The obturator (19) is movable in the passageway (2) between a first position within the passageway and a second position proximal of the first position and is constructed and arranged so that when in its first position it substantially covers in the direction of the longitudinal axis the distal end of the light emitting structure (7).

34 Claims, 5 Drawing Sheets

U.S. PATENT DOCUMENTS

| | | |
|---|---|---|
| 6,497,654 B1 | 12/2002 | Leonard et al. |
| 6,595,917 B2 | 7/2003 | Nieto |
| 7,244,228 B2 * | 7/2007 | Lubowski ............. 600/158 |
| 2002/0038075 A1 | 3/2002 | Tsai |
| 2002/0055670 A1 | 5/2002 | Weiss |
| 2005/0234299 A1 | 10/2005 | Eitenmuller et al. |
| 2005/0277811 A1 | 12/2005 | Richards et al. |
| 2006/0256575 A1 | 11/2006 | Vayser |
| 2007/0043264 A1 | 2/2007 | Gillis et al. |

FOREIGN PATENT DOCUMENTS

| | | |
|---|---|---|
| GB | 502331 | 3/1939 |
| GB | 1048600 | 11/1966 |
| IT | 1234169 | 6/1989 |
| WO | WO9825512 | 6/1998 |
| WO | WO03032821 | 4/2003 |
| WO | WO2004021874 | 3/2004 |
| WO | WO2005115223 | 12/2005 |
| WO | WO2006003122 | 3/2006 |
| WO | WO2006107877 | 10/2006 |
| WO | WO2006107878 | 10/2006 |
| WO | WO2006121530 | 11/2006 |
| WO | WO2006122031 | 11/2006 |
| WO | WO2007130276 | 11/2007 |

* cited by examiner

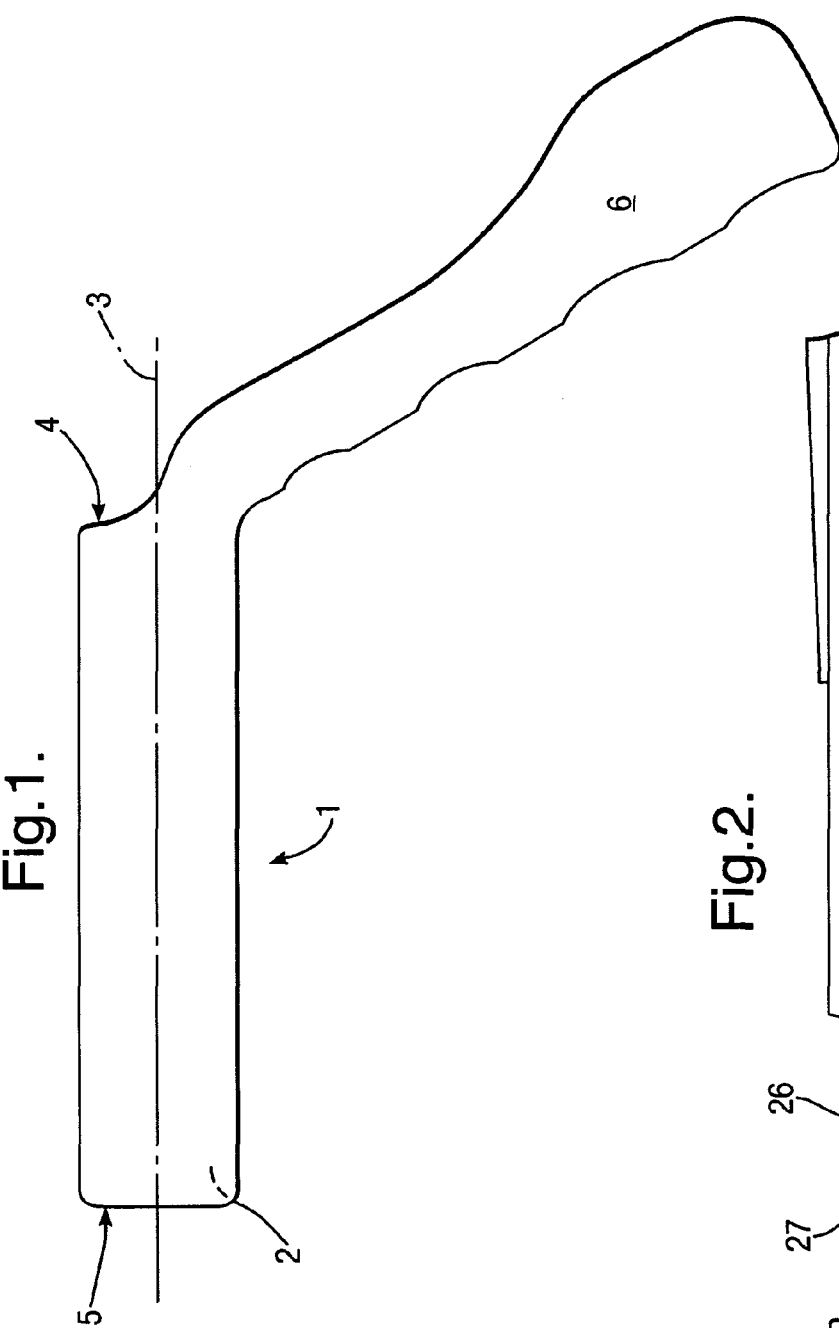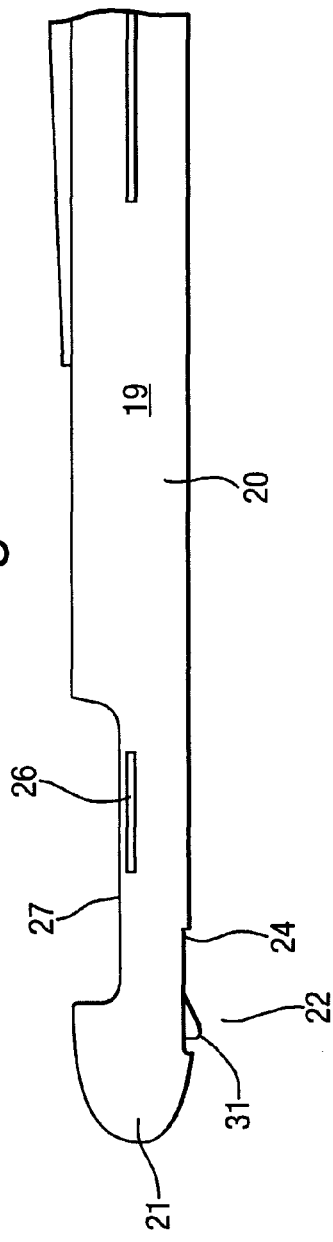

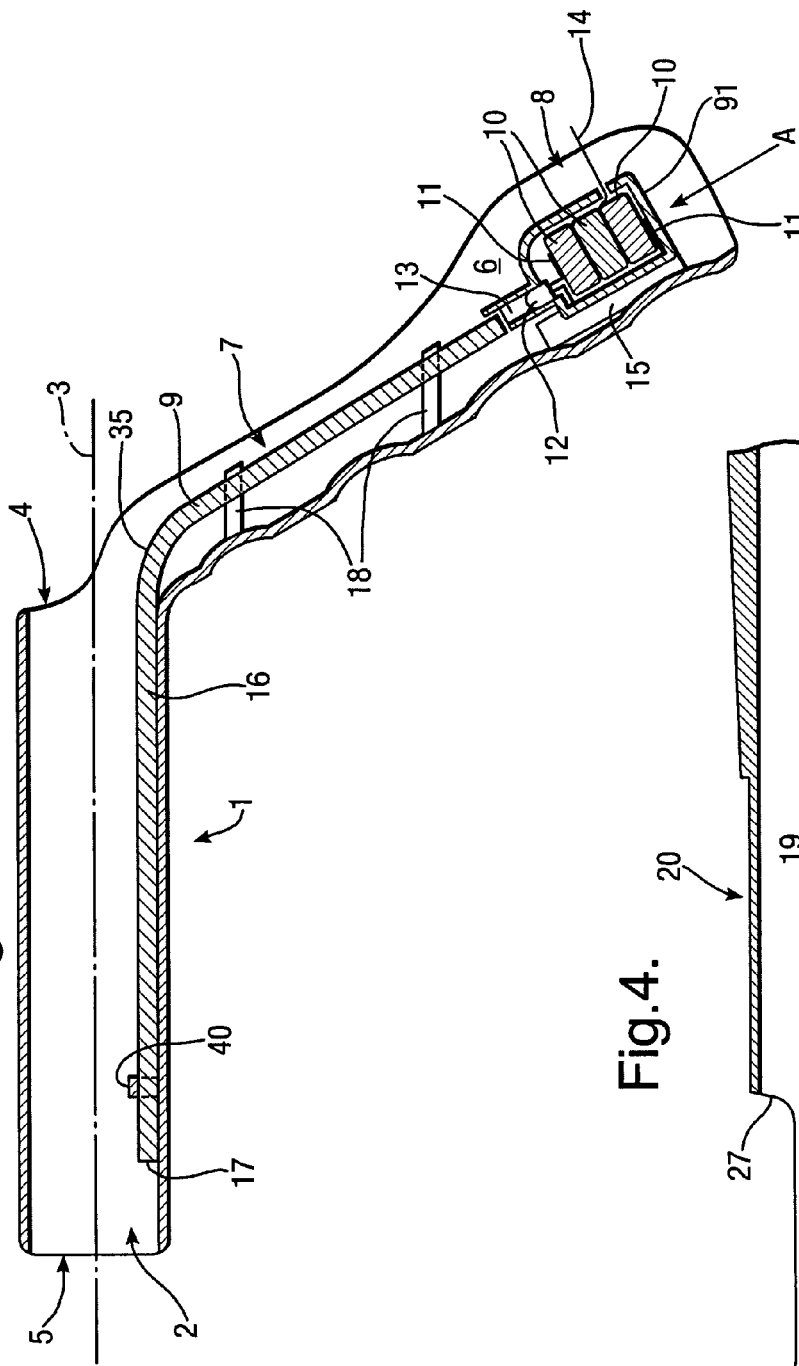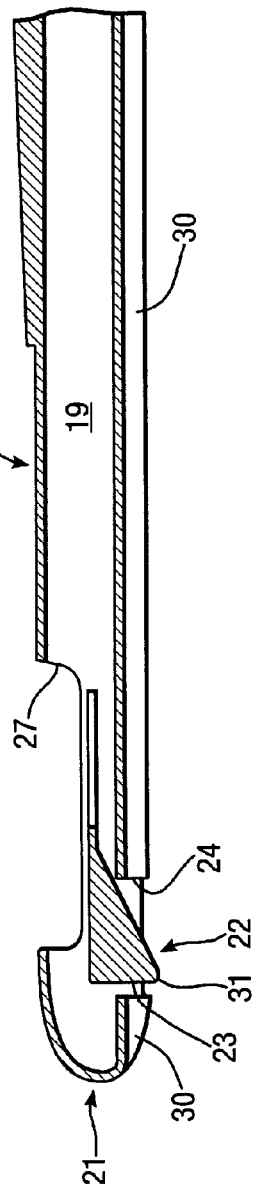

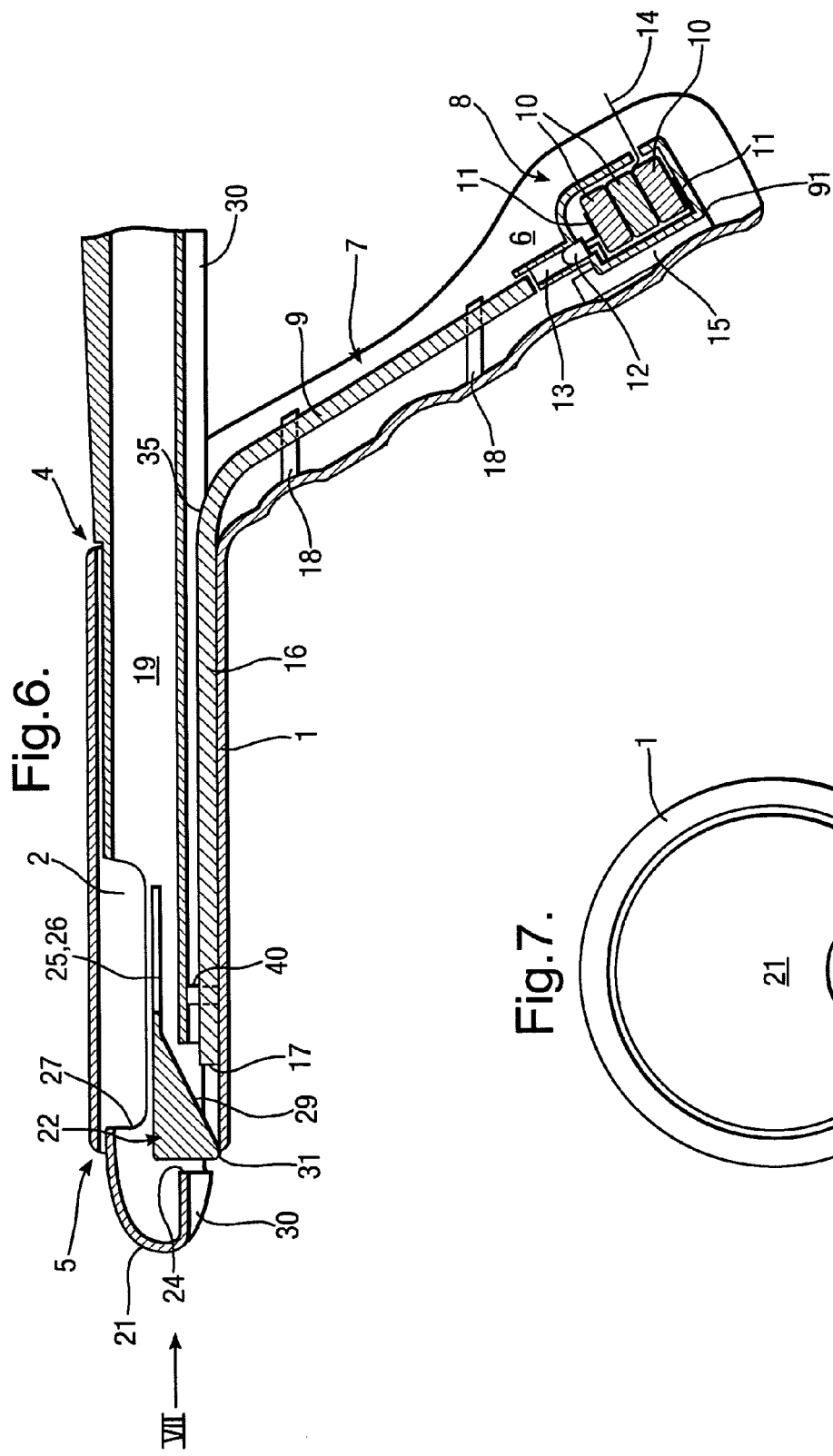
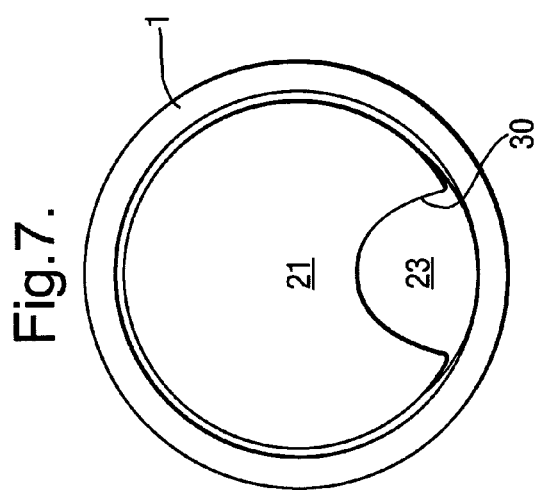

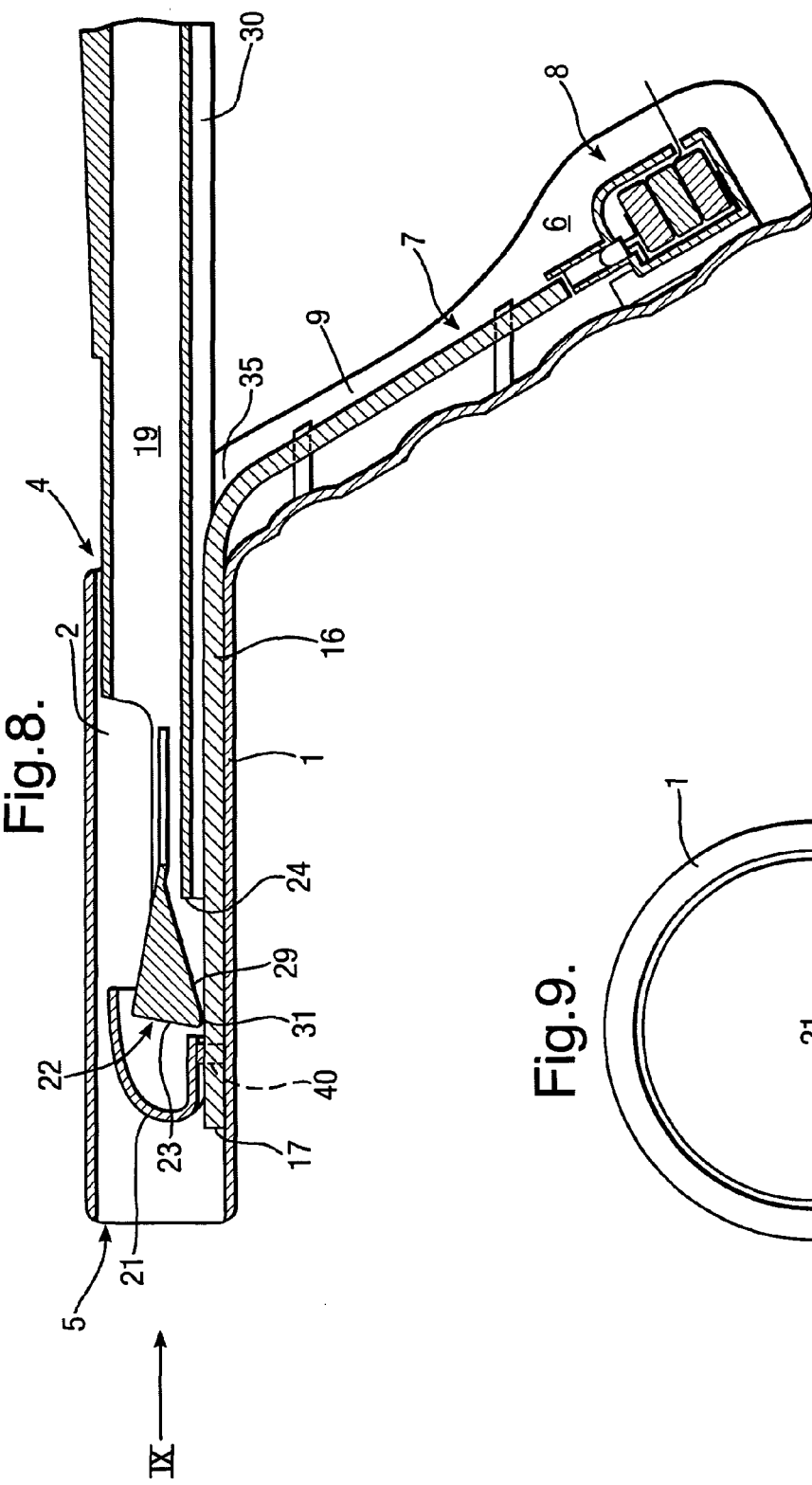

MEDICAL INSTRUMENTS

This is a national phase application of international application PCT/GB08/001,532, filed on May 2, 2008, claims the priority benefit of GB application no. 0708761.2 filed May 4, 2007, the contents of each are incorporated by reference.

This invention relates to illuminated medical instruments. The instruments are primarily intended to be used as medical speculum devices for insertion into body openings. The opening may be a naturally occurring opening such as the vagina or rectum, or an artificially created cavity such as a surgical wound. The invention is particularly suited to sigmoidoscopes and proctoscopes for insertion into the rectum, but it is not restricted to such applications.

Specula are commonly used to access openings in a body, such as a vagina, ear canal, mouth, rectum etc. In the case of the rectum, the instrument may be a proctoscope or a sigmoidoscope. Proctoscopes are shorter than sigmoidoscopes, and are commonly approximately 7.5 cm (3 inches) in length. Sigmoidoscopes are commonly approximately 25 cm (10 inches) in length. In both cases a light source is desirable to increase the accuracy of diagnostic examinations carried out using the scope and also to facilitate treatment processes carried out through the scope. In order to facilitate insertion of the scope into the body opening, the insertion portion of the scope usually has its passageway closed by a removable obturator.

It has previously been proposed to provide a sigmoidoscope with a removable light source. For example, GB Patent Number 1,048,600 (published 16 Nov. 1966) discloses the provision of a sigmoidoscope with a removable lighting unit. During initial insertion of the sigmoidoscope into the rectum the lighting unit is not present. Instead, a cylindrical obturator is fitted into the cylindrical passageway of the insertion portion of the sigmoidoscope so as to facilitate insertion into the rectum. Once insertion of the insertion portion into the rectum has been achieved, the obturator is removed and the lighting unit is attached to the sigmoidoscope. The lighting unit includes a housing, containing an electrical power source, that is mounted on the proximal end of the insertion portion. It also includes an elongate rod which extends from the housing into and along the passageway of the insertion portion, terminating near to the distal end of the passageway. At the end of the rod there is positioned a small prefocused electrical lamp. Electrical wiring is provided internally of the rod so as to connect the electrical power source to the electrical lamp. The need for the physician to assemble the lighting unit to the sigmoidoscope after both insertion of the sigmoidoscope into the rectum and removal of the obturator is undesirable. The lighting unit cannot, however, be mounted in the cylindrical passageway of the insertion portion of the sigmoidoscope prior to the scope's insertion into the body opening because it occupies space within the passageway, and would prevent the cylindrical obturator from being fitted into the passageway. The insertion portion cannot realistically be inserted into the anus without the obturator being fitted.

Other proposals have also been made for providing specula with lighting units. US Patent Application US 2007/0043264 A1 (published 22 Feb. 2007) discloses a scope having a lighting unit, provided at the proximal end of the insertion portion, comprising a pair of stubby light pipes which extend towards the proximal end of the passageway. An obturator, for fitment into the passageway, is provided with a pair of concave grooves on its external, otherwise generally cylindrical, surface. These grooves form channels in the passageway to allow light from the light pipes at the proximal end of the passageway to pass towards the distal end of the passageway. In order to allow light passing down the channels to exit the distal end of the insertion portion after its insertion into the body opening and with the obturator still present, the grooves provided in the obturator extend fully along the obturator and present a pair of distally facing openings at the distal end of the instrument. During insertion of the assembled instrument into the rectum for example, the combination of forward movement of the instrument and the presence of the distally facing openings at the distal tip of the instrument enables fluid or material, such as faeces, present in the rectum to be forced into the openings and along the channels. This fluid or material can make contact with and cover the end surfaces of the light pipes through which light is to be transmitted. Alternatively or additionally, withdrawal of the obturator can cause faeces in distal ends of the channels to be pulled back proximally onto the distally facing end portions of the light pipes. In both cases, the deposition of faeces on the distally directed ends of the light pipes severely degrades the lighting performance.

There is, thus, a need for a simple illuminated medical instrument in which a light emitting structure, arranged to direct light from the instrument into a body cavity, can be protected during insertion of the instrument into the body opening.

According to a first aspect of the present invention there is provided an illuminated medical instrument. The instrument may comprise an insertion portion for insertion into a body opening and defining an elongate passageway, the passageway extending along a longitudinal axis and having a proximal end and a distal end. It may also comprise an obturator for fitment into the passageway. It may also comprise a light emitting structure having a distal end arranged to direct light from the insertion portion into the body opening. The obturator may be movable in the passageway between a first position within the passageway and a second position proximal of the first position and be constructed and arranged so that when in its first position it substantially covers in the direction of the longitudinal axis the distal end of the light emitting structure According to a second aspect of the present invention there is provided an obturator for use in an illuminated medical scope. The obturator may be constructed and arranged to be movable distally, within a passageway provided through an insertion portion of the scope, to a distally advanced position in which it substantially covers a distal end of a light emitting structure associated with the insertion portion. In this position the obturator may substantially shield the distal end of the light emitting structure from soiling by contents of a body opening during insertion of the insertion portion into the body opening.

According to a third aspect of the present invention there is provided a method of protecting a light emitting structure of an illuminated medical scope. The method may comprise providing an obturator for slidable fitment into a passageway of an insertion portion of the scope and moving the obturator in a distal direction to a distally advanced position within the passageway in which position the obturator substantially covers, in the direction of movement, a distal end of the light emitting structure so as substantially to shield the distal end of the light emitting structure.

An embodiment of illuminated medical instrument in accordance with the present invention will now be described, by way of example only, with reference to the accompanying drawings, in which:

FIG. 1 is a side elevation of the insertion portion of an embodiment of proctoscope in accordance with the present invention;

FIG. 2 is a side elevation of an obturator for fitment into the passageway of the insertion portion of FIG. 1 (shown removed from the insertion portion);

FIG. 3 is a longitudinal section along the centre line of the insertion portion of FIG. 1;

FIG. 4 is a longitudinal section along the centre line of the obturator of FIG. 2;

FIG. 5b is a side elevation of the shielding structure of FIG. 5a, viewed in the direction of arrow VB in FIG. 5a;

FIG. 6 is a longitudinal section of the instrument of the earlier figures, showing the obturator of FIG. 2 fully distally advanced within the passageway of the insertion portion of FIG. 1;

FIG. 7 is a front end elevation (enlarged for clarity) of the distal end of the instrument of FIG. 6, showing the obturator fully distally advanced in the passageway of the insertion portion, viewed in the direction of arrow VII of FIG. 6;

Figure 5A:
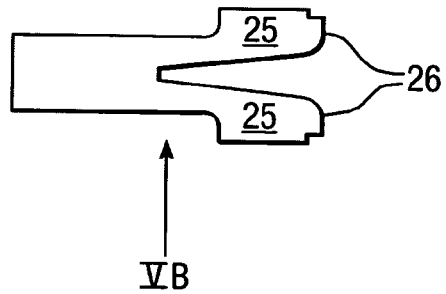
FIG. 5a is a top-plan view of the shielding structure of the obturator of FIGS. 2 and 4, showing the shielding structure removed from the main elongate portion of the obturator.

FIG. 8 is a view similar to FIG. 6, except that the obturator has been partially withdrawn within the passageway from the fully distally advanced position shown in FIG. 6; and FIG. 9 is a front end elevation (enlarged for clarity) of the distal end of the instrument of FIG. 8, with the obturator partially withdrawn from its fully distally advanced portion, viewed in the direction of arrow IX in FIG. 8.

FIG. 1 shows the insertion portion 1 of a proctoscope in side elevation. Although the present invention will be described in the context of a proctoscope, it may be applied to other illuminated medical instruments, including medical speculum devices such as sigmoidoscopes and vaginal specula. In addition, although the illustrated embodiment of the instrument is intended for insertion into a naturally occurring body opening such as the rectum, the invention is applicable to illuminated medical instruments for insertion into other naturally occurring body openings, such as the vagina, or artificially created cavities such as surgical wounds.

The insertion portion 1 defines an elongate passageway 2 therethrough. This passageway extends along a longitudinal axis 3 and has a proximal end 4 and a distal end 5. In this specification the term "proximal" means closest to the physician and "distal" means furthest from the physician. The elongate passageway 2 may be generally cylindrical in section or may, as shown, be slightly frusto-conical, tapering from the proximal end 4 towards the distal end 5. The insertion portion 1 is provided with a handle 6 at the proximal end 4 of the passageway 2. In the illustrated embodiment this handle 6 has a pistol grip arrangement.

The insertion portion 1 is provided with a light emitting structure 7 arranged to direct light from the insertion portion 1, via the open distal end 5 of the passageway 2, into a body opening in use. The light emitting structure 7 includes a light source 8 and a light pipe 9 that is arranged to convey illumination from the light source 8 to the distal end 5 of the passageway 2.

In the illustrated embodiment the light source 8 comprises a housing 9 containing three dry cell batteries 10 of the sort commonly found in electronic calculators. The batteries 10 are arranged in series and are sandwiched between a pair of electrical contacts, which contacts are connected to a white light Light Emitting Diode (LED) 12 mounted at the base of a conduit 13 at the upper end of the housing 9. A removable tag 14 of electrically insulating material is shown as being inserted between the two lowermost batteries 10 and extending outwardly from the housing 9. By grasping the end of the tag 14 and pulling it from the housing the electrical circuit formed by the batteries 10, contacts 11 and LED 12 can be switched from an open circuit condition to a closed circuit condition causing the LED 12 to illuminate.

In the illustrated embodiment the housing 9 of the light source 8 is provided with a shoe enabling the light source 8 to be slid onto (in the direction of arrow A in FIG. 3) a skid 15 moulded integrally with the handle 6. In this way, the light source 8, which may have a shelf life of only a few years due to it containing dry cell batteries 10, may be provided (in a sterile package) separately of the other components 1, 19 of the proctoscope (provided in a separate sterile package). Prior to the medical procedure involving use of the proctoscope, the physician may simply remove the proctoscope and the light source 8 from their respective sterile packs and slide the shoe of the housing 9 of the light source 8 onto the skid 15. The slid 15 and shoe co-operate to retain the light source 8 in position with the proximal end of the light pipe 9 coincident with the LED 12 and the conduit 13 so that illumination received from the LED 12 by the light pipe 9 is transmitted along the length of the light pipe 9 to the distal end 17 of the light pipe.

In the illustrated embodiment the light pipe 9 takes the form of a solid, cylindrical-section acrylic rod that is capable of transmitting light along its length. The rod may be made of other medically approved polymers that will transmit light, such as polyacrylates. Two supporting arms 18 are integrally moulded on the interior surface of the handle 6, each to grip the proximal half of the light pipe 9 and to retain it in position. The distal half 16 of the light pipe 9, which is mounted flush against the base of the cylindrical inner wall surface defining the passageway 2 of the insertion portion 1, is retained in position by passing under a hoop 40 integrally moulded with the wall of the insertion portion 1 (also visible in FIG. 9).

The distal end 17 of the light pipe 9 is arranged to direct light (emanating from the LED 12) from the interior of the passageway 2 of the insertion portion 1 into a body opening so as to enable a physician looking along the passageway 2 better to view target areas of interest within the body opening. In order to minimise light loss it will be noted that the distal end 17 of the light pipe 9 is positioned close to, but not at, the distal end 5 of the passageway 2, for example being set back therefrom by approximately 1-2 cm (0.4-0.8 inches). This helps to avoid unwanted loss of light but also protects the distal end 17 of the light pipe 9 from being easily soiled by contact with faeces in use when an obturator is no longer present.

Although not shown, an optical element may be provided distally of the distal end 17 of the light pipe 9 to receive light from the light pipe and to redirect that light. Such an optical element might comprise a diffuser or a polished surface to act as a mirror and might be integrally moulded with the wall of the insertion portion 1.

Although shown as being provided separately of the insertion portion 1, the light source 8 may be integrally provided with the insertion portion 1 if long shelf-life is not an issue, i.e. the complete scope may be provided pre-assembled in a single sterile package.

FIGS. 2 and 4 show an obturator 19 for fitment into the passageway 2 of the insertion portion 1 of FIGS. 1 and 3. The obturator 19 comprises a main elongate portion 20 which is arranged to be received in the passageway 2 and to be movable therein between a first, fully distally advanced position (shown in FIG. 6) and a second position proximal of that first position. The second position may be with the obturator 19 still partially received within the passageway 2 (as shown in FIG. 8), or it may involve the complete withdrawal of the obturator 19 from the proximal end 4 of the passageway 2.

The obturator 19 is provided with a generally rounded distal tip 21. In the first, fully distally advanced position of the obturator (shown in FIG. 6) the distal tip 21 extends from the distal end 5 of the passageway 2 to a position distally beyond the insertion portion 1 so as to facilitate insertion of the insertion portion of the assembled proctoscope (insertion portion and obturator 19) into a body opening.

Figure 5B:
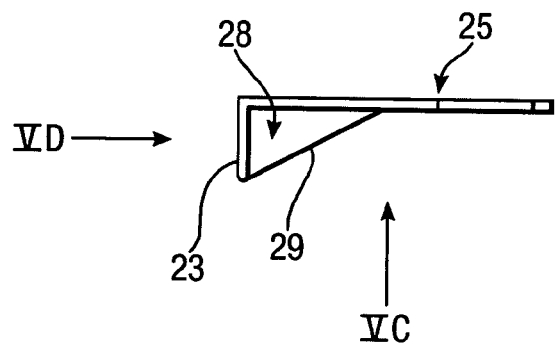
Figure 5C:
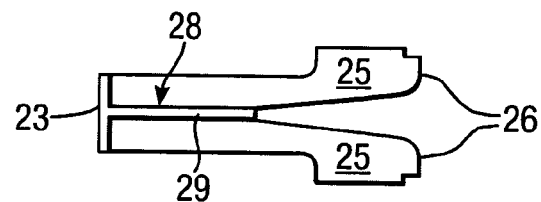
FIG. 5c is a plan view of the underside of the shielding structure of FIGS. 5a and 5b, viewed in the direction of arrow VC in FIG. 5b.
Figure 5D:
FIG. 5d is an end elevation of the shielding structure of FIGS. 5a-5c, viewed in the direction of arrow VD in FIG. 5c.

The obturator 19 is provided with a shielding structure 22 that is most readily visible in FIGS. 4, 6, 8 and 9. The shielding structure comprises a planar shield 23 which in use depends downwardly through an opening 24 provided in the lower wall of the otherwise hollow structure of the main elongate portion 20 of the obturator 19. At its base the planar shield 23 has a camming surface in the form of a rounded nose 31. As can be seen most readily in FIGS. 5a-5d, this planar shield 23 is provided on the distal end of a planar leaf-spring 25. At the proximal end of the leaf-spring 25 there are provided two tabs 26. By pinching the tabs 26 together and inserting the shielding structure 22 through an opening 27 provided in the top wall of the main elongate portion 20 of the obturator 19, the shielding structure 22 is installed in the position shown in FIG. 4, with the two tabs 26 each being sprung back out and locked into a correspondingly shaped elongate slot 31 provided in the wall of the main elongate portion 20 of the obturator 19.

In order to strengthen the planar shield 23 and the leaf-spring 25, a triangular web 28 is provided therebetween. As will be apparent from the discussion below, the lower facing edge of this web 28 forms a camming surface 29. It is envisaged that the shielding structure 22 will be moulded from a resilient plastics material so as to enable the leaf-spring 25 to bias the planar shield 23 to the default position illustrated in FIG. 4, so that upward movement of the planar shield 23 will be against the restoring bias of the leaf-spring 25.

Unlike a conventional, generally cylindrical proctoscope obturator, the obturator 19 of the illustrated embodiment is provided on its underside with a concave groove 30, which groove extends along the underside of the obturator 19, providing a portion of the groove 30 distally beyond the opening 24 provided for the shielding structure 22 and a (longer) portion of the groove proximally of that opening 24. As will be apparent from FIGS. 6 and 8, and from the following description, this concave groove 30 forms a channel to accommodate the distal half 16 of the light pipe 9.

The following is a description of a sequence of events involved in the insertion of the obturator 19 into the proximal end 4 of the passageway 2 of the insertion portion 1 and its advancement in the distal direction to the first, fully distally advanced position illustrated in FIG. 6. The obturator 19 may, however, be supplied to the physician pre-installed in the passageway 2. By approximately aligning the centre line (not shown) of the obturator 19 with the longitudinal axis 3 of the passageway 2 of the insertion portion 1, and then advancing the obturator 19 distally, the distal tip 21 of the obturator 19 is inserted into the proximal end 4 of the passageway 2. In this condition the outside surface 35 of the curved middle portion of the light pipe 9 can enter into the channel formed by the portion of the groove 30 formed in the distal tip 21 ahead of the shielding structure 22. Further distal advancement of the obturator 19 causes the rounded nose 31 provided at the base of the planar shield 23 of the shielding structure 22 to contact the outside surface 35 of the curved middle portion of the light pipe 9. The combination of the rounded shape for the nose 31 and the curvature of the outside surface 35 of the curved middle portion of the light pipe 9 causes the shielding structure 22 to be deflected upwardly, against the restoring bias of the leaf-spring 25, so that further distal advancement of the obturator 19 is achievable as a result of the rounded nose 31 of the planar shield 23 sliding along the top surface of the elongate distal portion 16 of the light pipe 9, as well as momentarily sliding further up and over the obstacle presented by hoop 40. Upon the rounded nose 31 being moved past a position of longitudinal alignment with the distal end 17 of the light pipe 9, the restoring bias of the leaf-spring 25 causes the shielding structure 22 to move laterally with respect to the longitudinal axis 3 of the passageway (in the downwards direction as drawn) to a position in front of (and covering) the distal end 17 of the light pipe 9. Continued distal advancement of the obturator 19 brings the obturator to the first, distally fully advanced position illustrated in FIG. 6. In this first position the rounded distal tip 21 of the obturator 19 extends distally beyond the distal end of the insertion portion 1, occluding the majority of the distal end 5 of the passageway 2, as shown in FIG. 7. Because, in this first position, the shielding structure 22 has been deflected downwardly to the position illustrated in FIG. 6, the planar shield 23 of the shielding structure 22 has the effect of at least substantially occluding the remainder of the distal end 5 of the passageway 2, covering the distal end 17 of the light pipe 9 in the direction of the longitudinal axis 3 of the passageway 2. This is why that distal end 17 is not visible in FIG. 7 but is in FIG. 9. As a consequence, when the assembled proctoscope, in the condition illustrated in FIG. 6, is inserted into a body opening such as the anus, the distal tip 21 and the planar shield 23 combine so as substantially completely to occlude the distal end 5 of the passageway. This assists in impeding the unwanted entry of contents of the body cavity into the passageway during the action of insertion of the insertion portion 1 into the body opening. Where the body opening is the anus, and the instrument is (as here) a proctoscope, this substantially prevents faeces from coming into contact with and soiling the distal end 17 of the light pipe 9.

Once the proctoscope has been fully inserted into the body opening the physician may wish to withdraw the obturator 19 from the passageway 2 in order to enable the interior of the body opening to be viewed through the passageway with the benefit of illumination provided by the light emitting structure 7. If so, starting with the components in the position illustrated in FIG. 6, the physician, whilst holding the handle 6 of the insertion portion 1 so as to hold the scope steady, pulls gently on the proximal end of the obturator 19 so as to commence withdrawing it from the first position in the proximal direction. As the obturator 19 is withdrawn, the camming surface 29 on the underside of the shielding structure 22 will come into contact with the top edge of the distal end 17 of the light pipe 9. Continued withdrawal of the obturator 19 past this point of first contact will cause the camming surface 29 and the distal end 17 to cooperate to deflect the shielding structure 22 upwardly against the bias of the leaf-spring 25. Continued withdrawal of the obturator 19 will cause the shielding structure 22 to be cammed upwardly and withdrawn proximally over the top surface of the distal portion 16 of the light pipe 9, including over the top of the hoop 40, enabling the obturator 19 to be fully removed from the passageway 2 of the insertion portion 1. FIG. 8 illustrates a second position of the obturator 19, proximally withdrawn from the first, fully distally advanced position illustrated in FIG. 6, in which the obturator 19 has been partially, but not fully, withdrawn from the passageway 2. In the second position illustrated in FIG. 8 it can be seen that the upwardly deflected shielding structure 22 is positioned above the light pipe 9. As can be seen most readily in FIG. 9, upward displacement of the shielding structure 22 uncovers the distal end 17 of the light pipe 9. Unlike in the first position of the obturator 1 illustrated in FIG. 6, in the second position illustrated in FIG. 8 the shielding structure 22 is no longer axially aligned with the distal end 17 in the direction of the longitudinal axis 3 of the passageway 2. This axis 3, although drawn as centred in the passageway 2, might just as well have been drawn at the base of the passageway 2 (parallel to the axis 3 as drawn) extending through the distal end 17 of the light pipe 9.

Continued withdrawal of the obturator 19 from the second position illustrated in FIG. 8 separates the obturator 19 from the insertion portion 1 with the insertion portion 1 left in position in the body opening, enabling the physician then to remove the tag 14 from the light source 8 so as to close the electrical circuit. This causes the LED 12 to illuminate and light from the LED 12 to be transmitted by the light pipe 9 along the length of the light pipe, to direct the transmitted light in the distal direction from the distal end 17 of the light pipe 9. Because the distal end 17 of the light pipe 9 was substantially covered (in the direction of the longitudinal axis) during the act of inserting the assembled insertion portion and obturator (with the obturator in its first position), the distal end 17 of the light pipe 9 should be comparatively free of soiling. Although liquids present in the body opening during insertion of the instrument may have penetrated past the shielding structure 22 to contact the distal end 17 of the light pipe 9, little or no solids should have. It is solids, and in particular sticky solids such as faeces, which are most troublesome if they come into contact with the distal end 17 of the light pipe 9 during insertion of the instrument into the body opening.

If, during manipulation of the insertion portion 1 following removal of the obturator 19, solid material from the body opening enters the distal end 5 of the passageway 2 to soil the distal end 17 of the light pipe 9, the obturator can very easily be reinserted into the passageway 2. By advancing the reinstated obturator 19 to its fully, distally advanced position any such solid material can be dislodged and the obturator once again removed.

After the physician has made the required diagnostic examination or treatment through the passageway 2, the insertion portion 1 is withdrawn from the body opening by pulling gently on the handle 6 in the distal direction. It is envisaged that all components of the scope be single-use components, in which case they would then usually be discarded for destruction by incineration.

In the first, distally advanced position of the obturator 19 illustrated in FIG. 6, the planar shield 23 of the shielding structure 22 is shown as being generally aligned with the distal tip of the insertion portion 1. Although this is preferred, because then the planar shield 23 acts more effectively to occlude the distal end 5 of the passageway 2, the planar shield 23 (in the first position of the obturator) may alternatively be forward of (or even rearward of) the distal tip of the insertion portion 1. As long as the shielding structure 22, in the first position of the obturator 19, is broadly in alignment (in the direction of the longitudinal axis 3 of the passageway 2) with the portion (in this case distal end 17) of the light emitting structure (in this case light pipe 9) to be shielded from unwanted contact with the contents of the body opening, the shielding structure 22 will contribute to reducing unwanted soiling of the light emitting structure by contents of the body cavity.

It is envisaged that the insertion portion 1 and obturator 19 would be moulded from a medically approved polymer such as a polypropylene or a polyacrylate. It is likely also that the housing 9 of the light source 8 would be moulded of the same plastics material.

Although, in the illustrated embodiments, the light pipe 9 is shown as a separate component which is attached to the passageway 2 and handle 6 of the insertion portion 1, it is envisaged that the light pipe 9 could be integrally formed with the remainder of the insertion portion, for example, by moulding of at least the relevant portion of the insertion portion in an optically transparent plastics material, to act as a light guide.

Although in the illustrated embodiments the light pipe 9 is shown as being additional to the wall defining the passageway 2 of the insertion portion 1, it is envisaged that the function of the light pipe 9 might be assumed by the material of the wall itself. A yet further alternative arrangement would be for the light pipe to be provided underneath, rather than above, the lowermost wall defining the passageway 2.

In both of these alternative possibilities the obturator would need to be constructed and arranged so that, when in the above discussed first position, it substantially covers in the direction of the longitudinal axis 3 of the passageway 2 the distal end of whatever acts as the light emitting structure, be it a discrete light pipe (either internally or externally of the passageway 2) or integrally formed within the wall defining the passageway 2.

Although in the illustrated embodiments the obturator 19 is advanced in and retracted from the passageway 2 purely by longitudinal movement along the longitudinal axis 3, this longitudinal movement may be combined with other movements. For example, by widening the groove 30 so as to allow the obturator 19, when inserted in the passageway 2, to be rotated around the longitudinal axis 3, such rotation might be used to rotate a portion of the distal tip 21 of the obturator to cover the distal end 17 of the light emitting structure 7 in the direction of the longitudinal axis. In such an arrangement the need for a shielding structure that is movable relative to the main elongate portion of the obturator 19 might be avoided.

In addition, although in the illustrated embodiment the shielding structure 22 is deflected transversely with respect to the longitudinal axis 3, with no significant longitudinal movement, it may instead be deflected mainly longitudinally. For example, if the rigid shielding structure 22 was to be replaced by a rubber wiper or squeegee-style element, the rubber element could be deflected rearwardly on insertion of the obturator into the insertion portion and forwardly on its removal. This would enable the rubber element to pass over the light emitting structure, yet still offer protection to the distal end 17 of the light emitting structure in the first position and/or wipe the distal end clean on removal of the obturator post-insertion into the body cavity.

The invention claimed is:

1. An illuminated medical instrument comprising:
an insertion portion for insertion into a body opening and defining an elongate passageway, the passageway extending along a longitudinal axis and having a proximal end and a distal end;
an obturator for fitment into the passageway; and
a light emitting structure terminating at a distal end, the distal end of the light emitting structure being located within the passageway and arranged to direct light out of the distal end of the passageway into the body opening;
wherein the obturator is movable in the passageway between a first position within the passageway and a second position proximal of the first position and is provided with a shielding structure that is constructed and arranged to slide longitudinally over the distal end of the light emitting structure as the obturator is advanced longitudinally in the passageway from its second position to its first position and then to move transversely with respect to the longitudinal axis so that, in the first position of the obturator, the shielding structure at least substantially covers the distal end of the light emitting structure when viewed in the direction of the longitudinal axis from the distal end of the passageway.

2. An instrument as claimed in claim 1, wherein when substantially covered in the direction of the longitudinal axis the distal end of the light emitting structure is substantially shielded from soiling by contents of the body opening during insertion of the insertion portion into the body opening.

3. An instrument as claimed in claim 1, wherein the light emitting structure is provided on the insertion portion.

4. An instrument as claimed in claim 3, wherein the light emitting structure extends along the interior of the passageway.

5. An instrument as claimed in claim 1, wherein the elongate passageway has a distal half and a proximal half and the distal end of the light emitting structure is located in the distal half.

6. An instrument as claimed in claim 1, wherein the insertion portion includes a wall defining the passageway and the light emitting structure extends along the passage coincident with the wall and in the direction of the longitudinal axis.

7. An instrument as claimed in claim 1, wherein the light emitting structure includes a light pipe extending along at least the majority of the length of the elongate passageway.

8. An instrument as claimed in claim 7, wherein the light emitting structure further includes an optical structure constructed and arranged to receive light from the light pipe and to redirect the light.

9. An instrument as claimed in claim 8, wherein the optical structure forms the distal end of the light emitting structure.

10. An instrument as claimed in claim 7, wherein the insertion portion is provided with a handle in the region of the proximal end of the passageway.

11. An instrument as claimed in claim 10, wherein the handle portion has a pistol grip arrangement, the light source is in use provided on the handle and the light pipe is curved in the region of the proximal end of the passageway so as to curve smoothly between the insertion portion and the handle.

12. An instrument as claimed in claim 1, wherein the obturator is provided with a longitudinal groove which, in the first position of the obturator, extends generally parallel to the longitudinal axis of the passageway and receives therein at least a portion of the light emitting structure.

13. An instrument as claimed in any on claim 1, wherein the light emitting structure has a proximal end arranged to receive light from a light source and is constructed and arranged to convey illumination from the light source to the distal end of the light emitting structure.

14. An instrument as claimed in claim 1, wherein the light emitting structure is constructed and arranged so that, in use and in the second position of the obturator, the light conveyed to the distal end of the light pipe is projected out of the distal end of the passageway to illuminate features of the body opening into which the insertion portion has been inserted.

15. An instrument as claimed in claim 1, wherein in its first position the obturator is fully distally advanced in the passageway.

16. An instrument as claimed claim 15, wherein in its second position the obturator is present in the passageway, but is proximally withdrawn relative to its first position.

17. An instrument as claimed in claim 1, wherein the obturator is movable along the longitudinal axis of the passageway and is provided with a shielding structure which, in the first position of the obturator, is positioned distally of the distal end of the light emitting structure and is at least partially in alignment with the distal end of the light emitting structure in the direction of the longitudinal axis, so as to protect the distal structure of the light emitting structure during insertion of the insertion portion into the body opening.

18. An instrument as claimed in claim 17, wherein the shielding structure includes a generally planar shield terminating in a camming surface that is arranged to slide over the light emitting structure as the obturator is moved in the passageway between its first and second positions.

19. An instrument as claimed in claim 17, wherein in the first position of the obturator the shielding structure is generally longitudinally aligned with the distal tip of the insertion portion so as substantially to occlude the distal end of the passageway and thereby to assist in impeding the entry of contents of the body opening into the passageway during insertion of the insertion portion into the body opening.

20. An instrument as claimed in claim 19, wherein in the first position of the obturator the shielding structure is positioned no more than 10 mm distally forward or rearward of the distal tip of the insertion portion.

21. An instrument as claimed in claim 17, wherein the obturator includes a main elongate portion to extend along the longitudinal axis of the passageway when fitted into the passageway and the shielding structure is movable relative to the main elongate portion.

22. An instrument as claimed in claim 21, wherein the shielding structure is arranged to move transversely with respect to the longitudinal axis as the obturator is moved from its first position towards its second position.

23. An instrument as claimed in claim 21, wherein the shielding structure is arranged to move generally radially with respect to the longitudinal axis as the obturator is moved from its first position towards its second position.

24. An instrument as claimed in claim 17, wherein the shielding structure is constructed and arranged to be positioned distally of the distal end of the light emitting structure in the first position of the obturator, in alignment with the distal end of the light emitting structure in the direction of the longitudinal axis.

25. An instrument as claimed in claim 17, wherein the shielding structure is arranged to extend generally transversely with respect to the longitudinal axis in at least the first position of the obturator.

26. An instrument as claimed in claim 17, wherein the shielding structure is biassed away from the centre of the passageway.

27. An instrument as claimed in claim 17, wherein the shielding structure is mounted on a leaf-spring, one end of the leaf-spring being rigidly mounted to the or a main elongate portion of the obturator and the shielding structure being provided at the opposite end of the leaf spring, whereby to cause the shielding structure to be movable in use generally transversely with respect to the longitudinal axis of the passageway and be subject to a biassing effect from the leaf-spring.

28. An instrument as claimed in claim 17, wherein the shielding structure is associated with a caroming surface to cause the shielding structure to slide over and to be deflected transversely with respect to the longitudinal axis by a camming action as the obturator is moved from its first position towards its second position.

29. An instrument as claimed in claim 1, wherein the obturator has a distal tip arranged to extend distally beyond the insertion portion in the first position of the obturator and the distal tip of the obturator, when viewed in end elevation from distally beyond the distal tip in the proximal direction of the longitudinal axis, is grooved to allow the obturator to be slid into the passage of the insertion portion over the light emitting structure, with the light emitting structure being arranged to pass through the groove as the distal tip of the obturator is slid past it.

30. An instrument as claimed in claim 29, wherein the groove is generally arcuate in longitudinal cross-section.

31. An instrument as claimed in claim 1 wherein the instrument is a proctoscope or sigmoidoscope.

32. A method of protecting a light emitting structure of an illuminated medical scope, the method comprising providing an obturator for slidable fitment into a passageway of an insertion portion of the scope, moving the obturator in a distal direction to a distally advanced position within the passageway, and moving a shielding structure associated with the obturator transversely with respect to the direction of movement so as at least substantially to shield a distal end of the light emitting structure in the distally advance position of the obturator.

33. A method of illuminating the interior of a body opening using an illuminated medical scope, the method comprising;
the method of claim 32;
inserting the insertion portion of the scope into the body opening with the obturator in its distally advanced position, said shielding of the distal end of the light emitting structure by the obturator substantially preventing soiling of the distal end of the light emitting structure by contents of the body opening during said insertion;
withdrawing the obturator in a proximal direction from the distally advanced position to uncover the previously shielding distal end of the light emitting structure; and
illuminating the interior of the body opening by directing light into the body opening from the light emitting structure.

34. A method of providing a substantially unsoiled light emitting structure in an illuminated medical scope, the method comprising;
the method of claim 32; and
subsequently moving the obturator within the passageway in a direction opposite to said distal advancement direction so as to uncover the distal end of the light emitting structure.

* * * * *